(12) United States Patent
Feazel

(10) Patent No.: US 6,733,974 B1
(45) Date of Patent: May 11, 2004

(54) METHODS AND COMPOSITIONS FOR DETECTION OF SPECIFIC GENETIC CONSTRUCTS IN PLANT TRANSFORMATION EVENTS

(75) Inventor: Rhonda J. Feazel, Brighton, IL (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 09/999,076

(22) Filed: Nov. 30, 2001

Related U.S. Application Data

(60) Provisional application No. 60/250,649, filed on Dec. 1, 2000.

(51) Int. Cl.[7] .......................... C12Q 1/68; C07H 21/02; C07H 21/04
(52) U.S. Cl. .......................... 435/6; 536/23.1; 536/24.3
(58) Field of Search .............................. 435/6; 536/23.1, 536/24.3

(56) References Cited

U.S. PATENT DOCUMENTS 5,352,605 A * 10/1994 Fraley et al.
5,530,196 A    6/1996 Fraley et al.

FOREIGN PATENT DOCUMENTS

WO    WO9914318    *  3/1999

OTHER PUBLICATIONS

P. Windels, et.al., Development of a line specific GMO detection method: A case study, Med. Fac. Landbouww, Univ of Gent 64/5b:459–462, 1999. Belgium.

* cited by examiner

*Primary Examiner*—Ethan Whisenant
(74) *Attorney, Agent, or Firm*—Grace L. Bonner; E. Clifford Lawson

(57) ABSTRACT

The present invention provides robust and specific compositions and methods of using the same, in the form of unique primers, amplicons and assays for detecting the presence of the nptII/35S genetic construct, as found in certain cotton lines and other genetically transformed plants.

12 Claims, No Drawings

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<221> NAME/KEY: misc_feature
<223> OTHER INFORMATION: primer npt35s-r1213

<400> SEQUENCE: 1
caagatgcct ctgccgacag t                                             21

<210> SEQ ID NO 2
<211> LENGTH: 21
<212> TYPE: DNA
<213> ORGANISM: Artificial Sequence
<220> FEATURE:
<221> NAME/KEY: misc_feature
<223> OTHER INFORMATION: primer npt35s-f894

<400> SEQUENCE: 2
tgcccagtca tagccgaata g                                             21

<210> SEQ ID NO 3
<211> LENGTH: 340
<212> TYPE: DNA
<213> ORGANISM: Artificial Sequence
<220> FEATURE:
<221> NAME/KEY: misc_feature
```

```
<223> OTHER INFORMATION: amplicon produced from cotton nptII/35S PCR
      assay

<400> SEQUENCE: 3
tgcccagtca tagccgaata gcctctccac ccaagcggcc ggagaacctg cgtgcaatcc      60
atcttgttca atcatgcgaa acgatcgtct agctagagat ccccgatctt gtagagagag     120
actggtgatt tcagcgtgtc ctctccaaat gaaatgaact tccttatata gaggaagggt     180
cttgcgaagg atagtgggat tgtgcgtcat cccttacgtc agtggaagta tcacatcaat     240
ccacttgctt tgaagacgtg gttggaacgt cttcttttc cacgatgctc ctcgtgggtg      300
ggggtccatc tttgggacca ctgtcggcag aggcatcttg                           340

<210> SEQ ID NO 4
<211> LENGTH: 428
<212> TYPE: DNA
<213> ORGANISM: Artificial Sequence
<220> FEATURE:
<221> NAME/KEY: misc_feature
<223> OTHER INFORMATION: amplicon produced from Cotton nptII/35S PCR
      assay

<400> SEQUENCE: 4
tgcccagtca tagccgaata gcctctccac ccaagcggcc ggagaacctg cgtgcaatcc      60
atcttgttca atcatgcgaa acgatccggg gaattcctcg acgtcgacgg atctgagcga     120
aaccctataa gaaccctaat tcccttatct gggaactact cacacattat tatgagaaa     180 atagagagag atagatttgt agagagagac tggtgatttc agcgtgtcct ctccaaatga     240
aatgaacttc cttatataga ggaagggtct tgcgaaggat agtgggattg tgcgtcatcc     300
cttacgtcag tggagatatc acatcaatcc acttgctttg aagacgtggt tggaacgtct     360 tcttttcca cgatgctcct cgtgggtggg ggtccatctt tgggaccact gtcggcagag      420
gcatcttg                                                             428

<210> SEQ ID NO 5
<211> LENGTH: 26
<212> TYPE: DNA
<213> ORGANISM: Artificial Sequence
<220> FEATURE:
<221> NAME/KEY: misc_feature
<223> OTHER INFORMATION: primer SQ31

<400> SEQUENCE: 5
ccgggttgaa attgggttca tttatg                                          26

<210> SEQ ID NO 6
<211> LENGTH: 25
<212> TYPE: DNA
<213> ORGANISM: Artificial Sequence
<220> FEATURE:
<221> NAME/KEY: misc_feature
<223> OTHER INFORMATION: primer SQ34

<400> SEQUENCE: 6
ccaccgtgat tccgaattct tcctc                                           25
```

US 6,733,974 B1

METHODS AND COMPOSITIONS FOR DETECTION OF SPECIFIC GENETIC CONSTRUCTS IN PLANT TRANSFORMATION EVENTS

CROSS REFERENCE TO RELATED APPLICATIONS

This application claims the benefit of priority to U.S. Provisional Application Serial No. 60/250,649, filed Dec. 1, 2000.

FIELD OF THE INVENTION

The present invention relates to the field of plant molecular biology, more specifically the invention relates to composition and assays for detecting the presence of specific genetic constructs in plant transformation events in a DNA sample from a cotton plant or other plant species.

BACKGROUND

Cotton is an important fiber crop in many areas of the world. The methods of biotechnology have been applied to cotton for improvement of the agronomic traits and the quality of the product. The method of introducing transgenes into cotton plants is demonstrated in U.S. Pat. No. 5,004,863. One such introduced DNA sequence important in cotton production is the cauliflower mosaic virus 35S promoter (CaMV35 or 35S) sequence. The promoter from the cauliflower mosaic virus is one of the most abundantly used genetic elements in genetically transformed crops. An important gene is the neomycin phosphotransferase sequence (nptII). The nptII sequence was originally isolated from the bacterial transposon 5. The nptII sequence has been used in many genetically transformed crops as a marker sequence. These DNA sequences have been introduced into cotton plants and are found in commercially available transformed varieties of cotton that are under production.

The expression of foreign gene sequences in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421–477, 1988). For a number of reasons, it is often desirable to screen for specific DNA sequences in order to confirm the presence of an event of interest. For example, it has been observed in plants and in other organisms that there may be a wide variation in levels of expression of an introduced genes among events. There may also be differences in spatial or temporal patterns of expression, for example, differences in the relative expression of a transgene in various plant tissues, that may not correspond to the patterns expected from transcriptional regulatory elements present in the introduced DNA construct(s). There is also an increasing interest in sampling lots of plant-based material for identity preservation, that is, to detect whether the material being tested contains any, all or no genetically-transformed plant material and/or the source of any transformed plant material identified in a given lot that is being tested or sampled. For this and other reasons, it is often desirable to screen or assay for a specific genetic transformation event.

One example of when it would be advantageous to be able to detect the presence of a particular event is in order to determine whether progeny of a sexual cross contain a transgene of interest. In addition, a method for detecting a particular event would be helpful for complying with various regulatory requirements, for example regulations requiring the premarket approval or labeling of foods derived from recombinant crop plants.

It is possible to detect the presence of a genetic transformation event by any well known nucleic acid detection method including DNA amplification methods, such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different genetic transformation events that possess more than one element, particularly those produced using the same DNA construct unless additional information is known. An event-specific PCR assay is discussed, for example, by Windels et al. (Med. Fac. Landbouww, Univ. Gent 64/5b:459–462, 1999), who identified glyphosate tolerant soybean event 40-3-2 by PCR using a primer set spanning the junction between the insert and flanking DNA, specifically one primer that included sequence from the insert and a second primer that included sequence from flanking DNA.

However, these currently available methods of detecting genetic transformation events in plant material involve the use of assays that are not specific or robust enough to differentiate among specific genetic transformation events. Commonly such previously available methods involve performing multiple detection assays, each assay specific for just one genetic construct or sequence, in order to detect the presence of transgenic DNA. For example, one assay for detection of the 35S promoter that is currently in use for detection of transgenic plant material is designed to detect the presence of the 35S promoter in a sample. The problem with this is that a sample can be positive for the 35S promoter in a detection assay if it contains any one of the commercial cotton genetic transformation events, or if the sample contains another of the at least twenty-two products that currently use the 35S promoter sequence, or if the sample has been contaminated with a virus that has a similar sequence to the 35S promoter (a false positive result). Such a 35S promoter detection assay is considered to be not specific enough to say with certainty the source identity of a positive result. An assay for the 35S promoter alone cannot definitively determine whether a sample that gives a positive result does contain, for example, a sample from a transformed cotton plant or represents some other transgenic sample or represents a plant infected by a virus with a similar sequence. To detect even the current commercial cotton genetic transformation events, at least three separate event-specific PCR assays would need to be performed. More specific PCR assays (with lower false positive levels) to detect the current commercial cotton transgenic events are still needed.

SUMMARY

A single assay to detect the presence of specific genetic transformation events in a sample lot of plant material such as cotton seed, the primers for such an assay and methods of using the assay are provided. DNA sequences are provided that comprise unique and advantageous primers that produce unique and unexpected target amplicons that span a junction sequence of an event comprising the 35S promoter and nptII coding sequences; the primers are identified as SEQ ID NO:1 and SEQ ID NO:2. Sequences highly homologous to these primers are also useful in the assay, as are the complements to each, as one would expect.

The invention accomplishes the designing of a single generic assay that detects all three of the current commercial cotton transgenic events and is more specific than current promoter or gene-specific assays. The assay methods also detect the presence of a DNA construct comprising the 35S promoter and nptII sequence in close proximity and in the same orientation in other species of plants.

The assay of the present invention uses one primer anchored in the 35S promoter and one primer anchored in the nptII sequence. The resulting amplicon of these primers span the junction region between the 35S promoter and the nptII sequence in the constructs. Different constructs of these elements will produce different amplicons. The constructs used in making the current cotton products were different and the present assay can differentiate between the two constructs used.

It is highly unlikely that any potential contaminants in a seed or other plant-material-containing sample other than from a transgenic source could produce a positive result using this assay since the 35S promoter sequence and nptII sequence are not found together in non-transgenic organisms. It was surprisingly discovered that although many primers can be generated to anchor in each element of the sequence, such primers usually are not specific and robust in their performance and produce both false positive results and/or false negative results to when used in an assay.

The primers of the present invention overcome this problem. The amplicons produced using these primers are specifically and robustly diagnostic for the nptII/35S construct used to make genetic transformation events. The amplicons produced by DNA primers homologous or complementary to SEQ ID NO:1 and SEQ ID NO:2 are an aspect of the invention.

According to another aspect of the invention, methods of detecting the presence of DNA corresponding to the nptII/35S DNA sequence in transgenic cotton or other plants, in a sample are provided. Such methods comprise: (a) contacting the sample DNA with a primer set comprising SEQ ID NO: 1 and SEQ ID NO:2 in a nucleic acid amplification reaction; (b) performing a nucleic acid amplification reaction, and (c) detecting the presence or absence of the amplicon.

These and other features, aspects, and advantages of the present invention will become better understood with regard to the following description and appended claims .

DETAILED DESCRIPTION OF THE PREFERRED EMBODIMENTS

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR § 1.822 is used.

As used herein, the term "cotton" means *Gossypium hirsutum* and includes all plant varieties that can be bred with cotton, including wild cotton species.

As used herein, the term "comprising" means "including but not limited to."

A transgenic "event" occurs with each independent transformation of plant cells with heterologous DNA, i.e., a nucleic acid construct that includes a transgene of interest; regeneration of a population of plants resulting from the insertion of the transgene into the genome of the plant; and selection of a particular-plant characterized by insertion into a particular genome location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) with a parental line that does not contain the inserted DNA.

A "probe" is an isolated nucleic acid to which is desirably attached a conventional detectable label or reporter moiety, e.g., a radioactive isotope, ligand, chemiluminescent agent, vitamin, steroid or enzyme. Such a probe is complementary to a strand of a target nucleic acid, in the case of the present invention, to a strand of genomic DNA from transformation event nptII/35S, whether from a cotton plant, other plant containing the event, or from a sample that includes DNA from the event. Probes according to the present invention include not only deoxyribonucleic or ribonucleic acids but also polyamides and other probe materials that bind specifically to the target event DNA sequence and can be used to detect the presence of that target DNA sequence.

"Primers" are isolated nucleic acids that can be annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 11 nucleotides or more in length, preferably 18 nucleotides or more, more preferably 21 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in *Molecular Cloning: A Laboratory Manual*, 2nd ed., vol. 1–3, ed. Sambrook el al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

The nucleic acid probes and primers of the present invention hybridize under stringent conditions to the nptII/35S target DNA sequence. Any conventional nucleic acid hybridization or amplification method can be used with the primers of the present invention to identify the presence or absence of DNA from the target, specific genetic transformation event in a sample.

Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al, In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In one exemplary embodiment, the nucleic acid primers of the present invention will specifically hybridize to a target portion of the nptII/35S event under moderately stringent conditions, for example at about 2.0×SSC and about 65° C. In another exemplary embodiment, the nucleic acid primers of the present invention will specifically hybridize to a target portion of the nptII/35S event under high stringency conditions.

Regarding the amplification of the target portion nucleic acid sequence (e.g., by PCR) using the primers of the present invention, "stringent conditions" are conditions that permit the primer pair to hybridize only to the target nucleic-acid sequence to which the primer pair comprising SEQ ID NO: 1 and SEQ ID NO: 2, would bind and preferably to produce the unique amplification product, the amplicon, in a DNA amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. The use of the term "amplicon" specifically excludes primer dimers that may be formed in the DNA thermal amplification reaction.

Nucleic-acid amplification can be accomplished by any of the various nucleic-acid amplification methods known in the art, including but not limited to the polymerase chain reaction (PCR), LCR, TAS, 3SR, NASBA RCA and Q.beta. amplification.

A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990 and *PCR Applications: Protocols For Functional Genomics*, ed. Innis et al., Academic Press, San Diego, 1999. These methods as well as other methods known in the art of DNA amplification may be used in the practice of the present invention. The sequence of the specific transformation event of interest, the nptII/35S sequence, in cotton or other species of plants, can be verified by use of the primers comprising SEQ ID NO: 1 and SEQ ID NO: 2 of the invention provided herein in any suitable DNA amplification assay.

The readout in the assay may be fluorescent or ELISA-based. A signal indicates presence of the nptII/35S DNA sequence from a transgenic event, due to successful amplification, hybridization, and evaluation.

Taqman® (PE Applied Biosystems, Foster City, Calif.) is described as a method of detecting and quantifing the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

DNA detection kits can be developed using the compositions disclosed herein and the methods well known in the art of DNA detection. The kits are useful for identification of a transgenic event, containing a nptII/35S DNA construct, in a sample. The kits contain DNA sequences homologous or complementary to SEQ ID NO:1 and to SEQ ID NO:2. These DNA sequences are used as primers in DNA amplification reactions, or as probes in a DNA hybridization method.

The transgene genetic elements referred to herein are the cauliflower mosaic virus 35S promoter (P-CaMV.35S (Odell, et al. *Nature* 313:810–812, 1985), operably connected to the neomycin phosphotransferase gene (NPTII) (Fraley et al. Proc Natl. Acad Sci USA 80:4803–4807, 1983).

The assay of the present invention preferably includes an internal control step comprising including primers derived from native cotton DNA. Production of an amplicon of known size from these primers is a check for proper functioning of the assay, e.g., the use of proper reagents and conditions. One set of such primers derived from native cotton DNA are SEQ ID NO: 5 and SEQ ID NO: 6. They produce an amplicon of approximately 600 base pairs which is easily separable from an amplicon of the transgenic DNA, which in the current cotton products would be either about 340 base pairs or 428 base pairs as discussed below.

After a general description of the present invention, the following specific examples are presented to further depict the same in a specific manner. These examples are provided by way of illustration, and are not in any way intended to limit the present invention. Therefore, these examples are not to be construed as to limit the scope of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1
Primer Pair Development and Validation.

The 35S-driven nptII constructs that were used to create currently available commercial cotton tralsgenic events (pMON10518 for Bollgard® cotton, pMON17136 for Roundup Ready® cotton, and pBRX75 for BXN cotton) were compared and used as the target sequence for designing the primer sequences and assays of the present invention. All three constructs had a 35S promoter derived from cauliflower mosaic virus (CaMV) in close proximity to the nptII gene in the same orientation. The junction region between the two in the construct used to make BXN cotton (pBRX75) differs from the other two constructs. The differences in the junction regions result in a longer amplicon when the pBRX75 sequence as compared to that produced by the other constructs. Eight different primer pair combinations were designed that would span the nptII/35S junction region. The primer pairs were evaluated and eliminated if they were lacking one or more of the following criteria: specificity, robustness, the ability to detect one contaminated seed in a pool of 300 seeds, the ability to be multiplexed with an internal control primer pair, and the ability to be easily detected. The primer pair of the invention that is used in the nptII/35S assay (npt35s-f894/r1213) met all of these criteria.

A primer design software program, may be used to aid in the initial development of primer pairs. Several pairs of primers were originally designed that were capable of amplifying the selected ntII35S target sequence. A number of the designed primers bound to multiple priming sites. Primers that were capable of binding to multiple priming sites were eliminated.

The initially designed primers pairs were tested to determine which pair produces the most specific and robust amplicon product. Each primer set was tested using the following outlined parameters for: a) master mix and b) a reaction set-up.

The master mix conditions are preferably and approximately the following: Sigma Taq DNA Polymerase is used at 0.25 unit per reaction. A 10×buffer containing 15 mM $MgCl_2$ (final concentration is 1.5 MM $MgCl_2$) is used. One set of event specific primers to be tested is used at a final concentration of 0.25 $\mu$M. Optionally, one set of internal control primers may be included at a concentration of 0.05 $\mu$M–0.1 $\mu$M. And a final volume of each reaction should preferably equal to 10 $\mu$l (384 well plates).

The reaction set up conditions are preferably and approximately the following:

Each initially designed primer set, (and optionally including an internal control primer set) was tested under typical DNA amplification cycling conditions using a BioOvenIII thermocycler oven, as set forth in TABLE 1 below.

TABLE 1

| CYCLING PARAMETERS | | |
|---|---|---|
| Cycle No. | Settings | Time |
| 1 | 94° C. | 3 minutes |
| 10 | 94° C. | 1 minute |
|  | 64° C. | 1 minute (decreases 1° C. each cycle) |
|  | 72° C. | 1 minute |
| 25 | 94° C. | 1 minute |
|  | 54° C. | 1 minute |
|  | 72° C. | 1 minute |
| 1 | 72° C. | 3 minutes |

The most specific primer pairs, that is, pairs that are specific and demonstrate the expected results with the template samples used, were selected for further tests to determine the maximum pooling size that could be utilized reliably when testing pools of seeds or other materials. The goal selected was to be able to detect one seed containing a specific genetic transformation event in a pool of 300 negative seeds.

Amplifications were performed on the template from the pooled samples using the master mix and cycling parameters described above.

Some of the initially designed primers evaluated showed pooling sensitivity up to a pool size of 300 (excluding the samples from the suspect pool). These primers were selected for further testing on a large number of samples, in this case at least 96 or more samples.

Many of the initially designed primer pairs failed the robustness evaluation. A high false negative rate for any designed primer was considered to be unacceptable.

For example, one of the initially designed primers was capable of detecting the nptII/35S event at a level of 1:300, but was not considered to be acceptably robust because of many failed reactions in the testing. Another pair of the initially designed primer pairs failed both the sensitivity and robustness evaluation, because the positive and negative controls amplified well, but the pooled samples failed to do so.

Any primer pair showing above 5% false negatives and/or positives was eliminated after the sensitivity/robustness evaluation was completed After the number of primers and assays was narrowed down to a few based on the specificity, pooling sensitivity, and robustness evaluations, continued testing of their sensitivity, robustness, and ease of scoring was done with the pairs multiplexed with an internal control. The same samples were used as in testing the pool sensitivity and robustness.

For example, one set of primers and assay unacceptably experienced a few failures for the selected transgene amplicon, and also had the unacceptable result of the amplicons being too close in size to easily score or evaluate the results.

The primer set of the present invention resulted in no failures in the samples that were known to be positive for the nptII/35S transgene. The amplicons were able to be separated on the gel. These primers were:

| Primer Name | | Primer Sequence |
|---|---|---|
| SEQ ID NO: 1 | [npt35s-r1213] | CAAGATGCCTCTGCCGACAGT |
| SEQ ID NO: 2 | [npt35s-f894] | TGCCCAGTCATAGCCGAATAG |

The pMON10518 and pMON17136 constructs, and the transgenic events that were created by using them, produce an amplicon of approximately 340 base pairs (SEQ ID NO: 3) using the primer pair of SEQ ID NO: 1 and SEQ ID NO: 2 in the assay of the present invention. The pBRX75 construct and the BXN event that was created using this construct, produce an amplicon of approximately 428 base pairs (SEQ ID NO: 4) using the same primer pair in this assay.

Example 2

Preparation of a Sample to be Tested.

An entire sample of cotton seed is placed into a mechanical grinding apparatus. The seed is ground until the final powder meets at least the following specifications: a) 90% (by weight) is smaller than 1 mm (passes through a #18 sieve); b) 50% (by weight) is smaller than 0.5 mm (passes through a #35 sieve); and c) 37% (by weight) is smaller than 0.25 mm (passes through a #60 sieve).

Approximately 0.1 g of ground seed from each pool to be sampled is transferred into a well of a 2.2 ml deep square well plate or into a microcentrifuge tube. Approximately 900 $\mu$l of the Extraction Buffer [100 ml 1M Tris, pH 8.0; 100 ml 0.5M EDTA, pH 8.0; 29 g NaCl; 1000 $\mu$l beta-Mercaptoethanol; 750 ml Deionized Water; and QS to 1000 ml] and 120 $\mu$l of 10% SDS is added to each well or tube containing the ground seed sample and the plate or tubes are then sealed. The contents are mixed thoroughly (mechanically with a bead beater or a paint shaker) for approximately over 1 minute.

The samples are then incubated at 60–65° C. for at least 20 minutes and then the plate or tubes are centrifuged at 2000 rpm in a KR422 floor model Jouan centrifuge for approximately 1 minute at room temperature, this removes the majority of the buffer and tissue that may be on the seal or lid. After the centrifugation the seal from the plate or the lid is removed from the tube. Approximately 300 $\mu$l of 5M Sodium Acetate [680 g Sodium Acetate Trihydrate; and QS to 1000 ml with Deionized Water] is added to the contents of each well and the plate or tube is resealed. The plate or tube is mixed vigorously (mechanically with a bead beater or paint shaker) for approximately 30–60 seconds.

The plates or tubes are incubated on ice (ice bath) for 20 minutes or longer, and then centrifuged at 3500 rpm for at least 15 minutes at approximately 4° C. until the supernatant is clear (a layer of particulate matter may be present on the surface). Approximately 400 $\mu$l of supernatant is pipetted into a new deep well plate or tube with care taken to avoid transfer of any solids with the liquid. Approximately 500 $\mu$l of Isopropanol is next added to each well or tube and the plate or tubes are again sealed. The contents of the plate or tubes are mixed by well by inverting (approximately 20 or more times) and then incubated for approximately a minimum of 30 minutes, but the plate or tubes can be left overnight at −20° C. at this step.

The DNA is then pelleted by centrifuging the plate or tubes at 3500 rpm for approximately 10 minutes at 4° C., at the end of the centrifuigation, the supernatant is poured off and the pellet is drained, preferably by keeping the plate or tube inverted on absorbent paper for 2–5 minutes.

The plate or tubes are then placed top up to allow the DNA pellet to air dry to the point where any standing liquid is gone. Approximately 250 $\mu$l of 10:1 TE Buffer [10 ml 1M Tris-HCL at pH of 8.0; 2 ml 0.5M EDTA, at a pH of 8.0 and QS to 1000 ml (1 liter) with HPLC Water] is then pipetted into each well or tube to dissolve the DNA pellets. In the case where any solids remain after dissolving the pellet, the solids are centrifuged at approximately 3500 rpm for approximately 5 minutes and transfer the buffer is transferred to a new plate or tube leaving the solids behind. Approximately 28 $\mu$l of 3M Sodium Acetate and 450 $\mu$l of Isopropanol are pipetted into each well or tube and the plate or tubes are sealed and the contents are mixed by inverting (approximately 20 or more times). The plate or tubes are then incubated at approximately −20° C. for approximately 30 minutes.

The DNA is then pelleted by centrifuging the plate or tubes at 3500 rpm for approximately 10 minutes at 4° C., at the end of the centrifugation, the supernatant is poured off and the pellet is drained, preferably by keeping the plate or tube inverted on absorbent paper for 2–5 minutes.

The plate or tubes are then placed top up to allow the DNA pellet to air dry to the point where any standing liquid is gone. Approximately 250 $\mu$l of 10:1 TE Buffer [10 ml 1M Tris-HCL at pH of 8.0; 2 ml 0.5M EDTA, at a pH of 8.0 and QS to 1000 ml (1 liter) with HPLC Water] is then pipetted into each well or tube to dissolve the DNA pellets and the plate or tubes are again sealed.

DNA is ready for diluting to a concentration of 5–50 ng/$\mu$l for PCR or a concentration suitable for another selected DNA amplification method, after dissolving overnight at 4° C. Normal concentrations of DNA from this extraction should be above 500 ng/$\mu$l after dissolving the pellet in 100 $\mu$l 10:1 TE.

Adding approximately 3 $\mu$l or less of the stock DNA to approximately 100 $\mu$l of 10:1 TE Buffer will produce the desired concentration for use as a PCR template if the DNA yields are adequate. This stock is then preferably stored at approximately 4° C. or −20° C.

Example 3

Amplification of the Sample Prepared in Example 2.

A suitable reaction volume, for example 2.0 $\mu$l of DNA Template Dilution (5–50 ng/$\mu$l), 6.7 $\mu$l of HPLC Water; and 1.0 $\mu$l of 10×PCR Buffer containing 15 mM MgCl$_2$. Primers of SEQ ID NO: 1 and SEQ ID NO: 2, each in the amount of 0.025 $\mu$l(100 uM) and optionally and preferably 0.005 $\mu$l each of control primer sequences (SEQ ID NO: 5 and SEQ ID NO: 6); 0.2 $\mu$l of Nucleotide Mix (10 mM); and 0.05 $\mu$l of Taq Polymerase (5U/$\mu$l), for a total volume of 10.0 $\mu$l.

For a 10 $\mu$l reaction, 8 $\mu$l of the bulk reaction mix is pipetted into each well of a 384 well PCR plate(s). The plates are then centrifuged at approximately 2500 rpm for approximately 1 minute at approximately 4° C. to remove air bubbles. Approximately 2 $\mu$l of DNA solution from the template dilution plates or tubes is transferred into the appropriate wells of the PCR plate that contain the reaction mix. Both the PCR plate and the dilution plates or tubes are then sealed. The sealed PCR plates are then centrifuged at approximately 2500 rpm for approximately 1 minute at 4° C. The sealed PCR plates are then placed in the thermocycler using the same cycling parameters shown in Table 1 above. After the program is complete, remove the plate(s) from the thermocycler. Store the PCR plates at 4° C. until the amplification products can be electrophoresed.

Example 4

Electrophoresis of the Amplicons Generated in Example 3.

The amplification products are then loaded into a gel for electrophoresis, the technique of which is well know to one skilled in the art. Briefly, 10×TBE Buffer is diluted to 1×concentration with the Deionized water and 1.5% Agarose gels are made and poured into the appropriate number of gel molds and combs are inserted and the gels solidify at room temperature for at least 30 minutes before removing the combs or the molds. The PCR plates are centrifuged at approximately 2500 rpm for approximately 1 minute and the seal is then removed from the plate. Approximately 3 μl of 5×Sample Gel Buffer/loading dye [5.0 ml of 1M Tris-HCL, at pH of 8.0; 50.0 ml of Glycerol; 1.0 ml of 0.5M EDTA, at pH of 8.0; 2.5 ml of 10% SDS Solution; ~3.0 ml of Bromphenol Blue/Xylene Cyanole solution; 40.0 ml of HPLC Water] is added to each sample, and the entire volume is loaded into a well on the gel. At least one well of each comb is filled with 1.5 ml of a suitable PCR Marker, (in this case Sigma, St. Louis, Mo.) and the gel is electrophoresed at a setting of approximately 100 Volts for approximately 45 minutes. The gel is then photographed under UV light and evaluated.

Example 5

Evaluation of the Electrophoresed Amplification Products.

The following size products are possible for each cotton sample positive for the specific nptII/35S genetic transformation event, including the internal control produced by the use of primers of SEQ ID NO: 5 and SEQ ID NO:6.

| Transgene Assay | Product Size (base pairs) |
| --- | --- |
| 35S/nptII | 340 (Monsanto RR and BT) |
| 35S/nptII | 428 (BXN47) |
| Internal Control | 600 |

Negative cotton (non-transformed cotton) samples will lack intense bands at 340 and 428 basepairs. Samples producing a band of 340 and/or 428 base pairs are positive for one or more of the commercial genetic transformation events.

Having illustrated and described the principles of the present invention, it should be apparent to persons skilled in the art that the invention can be modified in arrangement and detail without departing from such principles. We claim all modifications that are within the spirit and scope of the appended claims.

It is to be understood that the present invention has been described in detail by way of illustration and example in order to acquaint others skilled in the art with the invention, its principles, and its practical application. Particular aspects and methods of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

What is claimed is:

1. An isolated DNA sequence consisting of the sequence of SEQ ID NO:1 or its complement.

2. An isolated DNA sequence consisting of the sequence of SEQ ID NO:2 or its complement.

3. An isolated DNA sequence consisting essentially of an amplicon produced by using a pair of primers comprising SEQ ID NO: 1 and SEQ ID NO: 2 as primers in a DNA amplification method wherein the primers are combined in the assay with plant material containing an nptII/35S DNA construct in a genetic transformation event.

4. A pair of isolated DNA sequences having a first sequence and a second sequence, wherein the first sequence comprises about 11 or more contiguous nucleotides of SEQ ID NO:1 or a complement thereof and wherein the second sequence comprises about 11 or more contiguous nucleotides of SEQ ID NO:2 or a complement thereof.

5. A DNA detection kit specific for an nptII/35S DNA construct comprising at least one DNA molecule of about 11 or more contiguous nucleotides of SEQ ID NO:1 or a complement thereof and at least one DNA molecule of about 11 or more contiguous nucleotides of SEQ ID NO:2 or a complement thereof.

6. The DNA detection kit of claim 5 wherein the kit further comprises an element selected from the group consisting of radionuclides, fluorophores, fluorochromes, peptides, enzymes, antigens, antibodies, chemiluminescent moieties, vitamins, and steroids.

7. The DNA detection kit of claim 5 wherein the kit further comprises a third DNA molecule comprising SEQ ID NO: 5 and a fourth DNA molecule comprising SEQ ID NO: 6.

8. A method of detecting the presence of DNA corresponding to the nptII/35S genetic construct in a sample of DNA extracted from plant material comprising:
 (a) contacting said sample with a primer pair comprising SEQ ID NO: 1 and SEQ ID NO: 2;
 (b) performing a nucleic acid amplification reaction; and
 (c) detecting the presence or absence of at least one amplicon of about 300 to about 450 basepairs.

9. The method of claim 8 wherein said plant material is from cotton and wherein an internal control is included wherein step (a) further comprises contacting said sample with a primer pair comprising SEQ ID NO: 5 and SEQ ID NO: 6 and step (c) further comprises detecting the presence of an amplicon of about 600 base pairs.

10. A method of detecting the presence of DNA corresponding to the nptII/35S genetic construct in a sample of plant material comprising:
 (a) contacting said sample with a pair of primers comprising SEQ ID NO: 1 and SEQ ID NO: 2;
 (b) subjecting the sample and probe to stringent hybridization conditions; and
 (c) detecting hybridization of the probe to the DNA.

11. A method of detecting the presence of DNA corresponding to the nptII/35S genetic construct in a sample of DNA extracted from cotton plant material comprising:
 (a) contacting said sample with a primers comprising SEQ ID NO: 1, SEQ ID NO: 2, SEQ ID NO: 3, and SEQ ID NO: 4;
 (a) performing a nucleic acid amplification reaction; and
 (b) detecting the presence or absence of at least one amplicon of about 300 to about 450 basepairs and the presence of an amplicon of about 600 basepairs.

12. The method of claim 11 wherein said cotton plant material is cotton seed.

\* \* \* \* \*